(12) United States Patent
Johnson et al.

(10) Patent No.: US 8,313,953 B2
(45) Date of Patent: Nov. 20, 2012

(54) SAMPLE COLLECTION SYSTEM AND METHOD

(75) Inventors: Robert S. Johnson, Hamstead, NH (US); Stephen Scheufele, Boylston, MA (US)

(73) Assignee: Horizon Technologies, Inc., Salem, NH (US)

( * ) Notice: Subject to any disclaimer, the term of this patent is extended or adjusted under 35 U.S.C. 154(b) by 0 days.

(21) Appl. No.: 13/401,067

(22) Filed: Feb. 21, 2012
(Under 37 CFR 1.47)

(65) Prior Publication Data

US 2012/0144897 A1    Jun. 14, 2012

Related U.S. Application Data

(63) Continuation of application No. 12/298,937, filed on Oct. 29, 2008, now Pat. No. 8,124,422, which is a continuation of application No. PCT/US2007/067950, filed on May 1, 2007.

(60) Provisional application No. 60/746,105, filed on May 1, 2006.

(51) Int. Cl.
*G01N 30/04* (2006.01)
*G01N 30/02* (2006.01)
*G01N 30/00* (2006.01)

(52) U.S. Cl. .......... 436/174; 436/175; 422/50; 422/500; 422/501; 73/23.41; 73/23.35; 73/23.2

(58) Field of Classification Search ................. 436/174, 436/175; 73/23.41, 23.35, 23.2; 422/101, 422/102, 50, 500, 501
See application file for complete search history.

(56) References Cited

U.S. PATENT DOCUMENTS

| | | | | |
|---|---|---|---|---|
| 5,150,601 A * | 9/1992 | Simeroth et al. | ............. | 73/23.41 |
| 5,217,619 A * | 6/1993 | Redmond et al. | ............. | 210/650 |
| 5,792,425 A * | 8/1998 | Clark et al. | ................. | 422/535 |
| 6,605,474 B1 * | 8/2003 | Cole | ............................. | 436/177 |
| 6,749,755 B2 * | 6/2004 | Johnson | ........................ | 210/650 |

* cited by examiner

*Primary Examiner* — Christine T Mui
(74) *Attorney, Agent, or Firm* — Grossman, Tucker, Perreault & Pfleger, PLLC

(57) ABSTRACT

An apparatus or method for removing water and concentrating an analyte in solution, wherein the concentrated analyte sample is delivered directly to a vial, such as an autosampler vial that is capable of use in a gas chromatography autosampler.

20 Claims, 4 Drawing Sheets

SAMPLE COLLECTION SYSTEM AND METHOD

CROSS REFERENCE TO RELATED APPLICATIONS

The present application is a continuation of International Application No. PCT/US07/67950 filed May 1, 2007 and published Nov. 15, 2007 as International Publication No. WO2007/130991, designating the United States, and which claims the benefit of the filing date of U.S. Provisional Application Ser. No. 60/746,105, filed May 1, 2006, the teachings of which are incorporated herein by reference.

FIELD OF THE INVENTION

The present disclosure generally relates to the collection and handling of samples for analysis, and more particularly directed at the collection of samples from an evaporative concentrator system.

BACKGROUND OF THE INVENTION

When samples need to be analyzed for trace organic compounds, the samples are typically extracted with an organic solvent. Due to selective chemistry, the organic solvents extract organic compounds from the sample. Extracted compounds, referred to as analytes, typically cannot be analyzed until residual water is removed from the solvent and the solvent is evaporated down in volume. Residual water in the solvent should be removed because it may have an adverse effect on compound analysis. The solvent should be evaporated down in volume to ensure the analytes are present in a concentration within the detection range of the analytical instrument used for analysis. The individual processes of extraction, removal of residual water, and evaporation are time consuming and operator dependent, thereby typically providing inconsistent recovery of analytes. Loss of analytes due to continual evaporation in unsealed commercial evaporation units may also contribute to inconsistent analyte recovery. Additionally, the need to transfer sample from an evaporation unit to an analytical instrument may increase the risk of loss and contamination of the sample.

SUMMARY OF THE INVENTION

The present disclosure relates in one exemplary embodiment to an apparatus for removing water and concentrating an analyte in a solvent comprising a reservoir for containing a first solution of solvent, residual water and an analyte sample, the reservoir having an opening to drain from the reservoir and a hydrophobic membrane layer comprising fluoropolymer material, said membrane layer positioned in series with said opening. A vessel then may be supplied for containing a second solution passed through said membrane, wherein said vessel is capable of reducing the solvent level of said solution. A sample collection vial may be directly connected to the vessel, such as a vial capable of use in a gas chromatography collection autosampler.

The present disclosure also relates in another exemplary embodiment to an apparatus for collecting and handling an analyte sample in solution for analysis. The apparatus includes a first section for removing water from the sample solution and a second section connected to the first section for concentrating the sample in the solution. The second section may also include a neck portion wherein the neck portion is configured to be engaged to a sample collection vial wherein the sample collection vial is capable of providing a sample to, e.g. an automated gas chromatography system.

BRIEF DESCRIPTION OF THE DRAWINGS

Features and advantages of the present invention are set forth through the description of exemplary embodiments consistent with the present invention, which description should be read in conjunction with the accompanying drawings, wherein.

DETAILED DESCRIPTION OF THE INVENTION

The present invention provides a system and method for collecting and handling a sample to be analyzed, e.g. via gas chromatography, mass spectroscopy, etc. The sample size for such testing may generally be relatively small, and may require a specified level of sample purity or concentration. Accordingly the sample may undergo concentration to remove water and excess solvents, e.g., from an extraction process, contaminants, etc., as well as to increase the concentration of the sample. Consistent with the present invention, the sample may be directly concentrated to a desired level or volume directly into a sample vial, e.g., for use with an analytical instrument.

Figure 1:
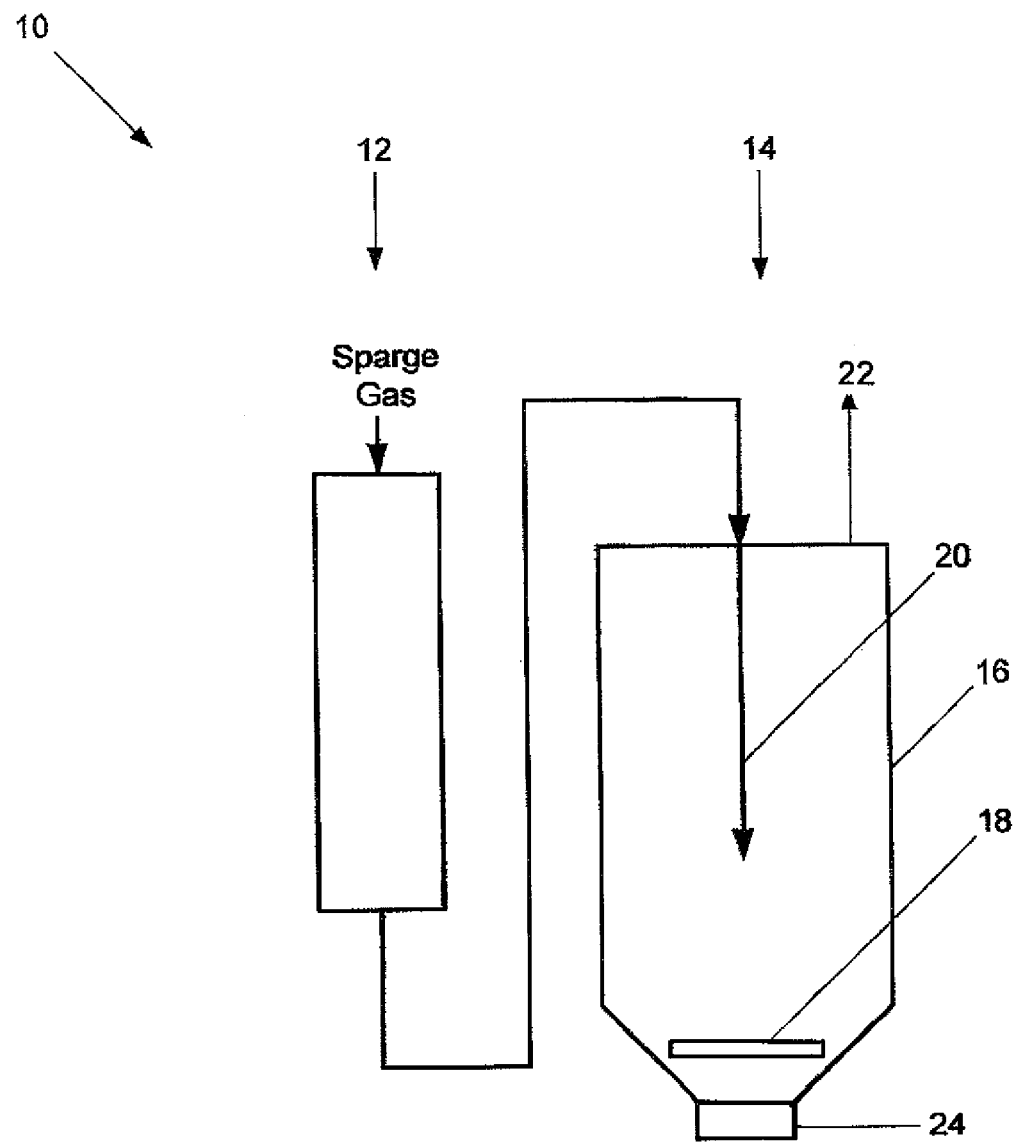
FIG. 1 schematically depicts an embodiment of an evaporative concentration system which may be used in connection with the present invention.

Referring to FIG. 1, according to one embodiment a sample may be collected directly from an evaporative concentration system 10. The evaporative concentration system 10 may generally provide a relatively concentrated sample and facilitate the removal of excess solvents, etc. As shown, in one embodiment, the evaporative concentration system 10 may generally include a first stage 12 for drying the sample, e.g., removing water from the sample. Water removal may be achieved using chemical drying agents, e.g., sodium sulfate, vacuum, dry gas sparging, membrane separation, etc. The dried sample may then be concentrated, e.g., excess solvent may be removed, etc.

Attention is therefore first directed to U.S. Pat. No. 6,749,755 whose teachings are incorporated herein by reference. As disclosed therein, an apparatus and method may be provided for separating residual water from a solvent. The device may comprise a reservoir containing a solution comprising solvent containing residual water, the reservoir having an opening to allow the solution to drain from the reservoir. A membrane layer may the be provided comprising a layer of fluoropolymer material, wherein the membrane material has an IPA Bubble Point of greater than or equal to 25 psi. The membrane may be positioned in series with the reservoir opening. Vacuum may be generated on one side of the membrane layer wherein the solvent containing water may pass through the membrane layer therein removing water from the solvent to provide a solvent with a water level of less than or equal to 1 ppm.

Attention is also directed to U.S. application Ser. No. 11/190,513 whose teachings are also incorporated herein by reference. As disclosed therein, an apparatus and method may be provided for separating water from a solvent and removing the solvent. The method may include providing a solution containing solvent and residual water and an analyte. The solution may be passed through a membrane to reduce water content wherein an analyte is present at a first concentration. This then may be followed by removing solvent from the solution. The membrane may again comprise a material having an IPA Bubble Point of greater than or equal to 25 psi. In particular, the membrane may include a hydrophobic membrane layer comprising a fluoropolymer material. The water content may also be reduced to less than or equal to 1.0 ppm.

Accordingly, the dried sample may be supplied to a second stage 14 for concentrating the sample, removing excess solvent, etc. For example, the sample may be delivered to an evaporation tube 16, which may include a heater 18, a supply of sparge gas 20, as well as a vacuum takeoff 22. A combination of heat, sparge gas and vacuum may be used to evaporate the solvent from the sample. The concentrated sample may be collected in a lower region 24 of the evaporation tube 16.

Figure 2:
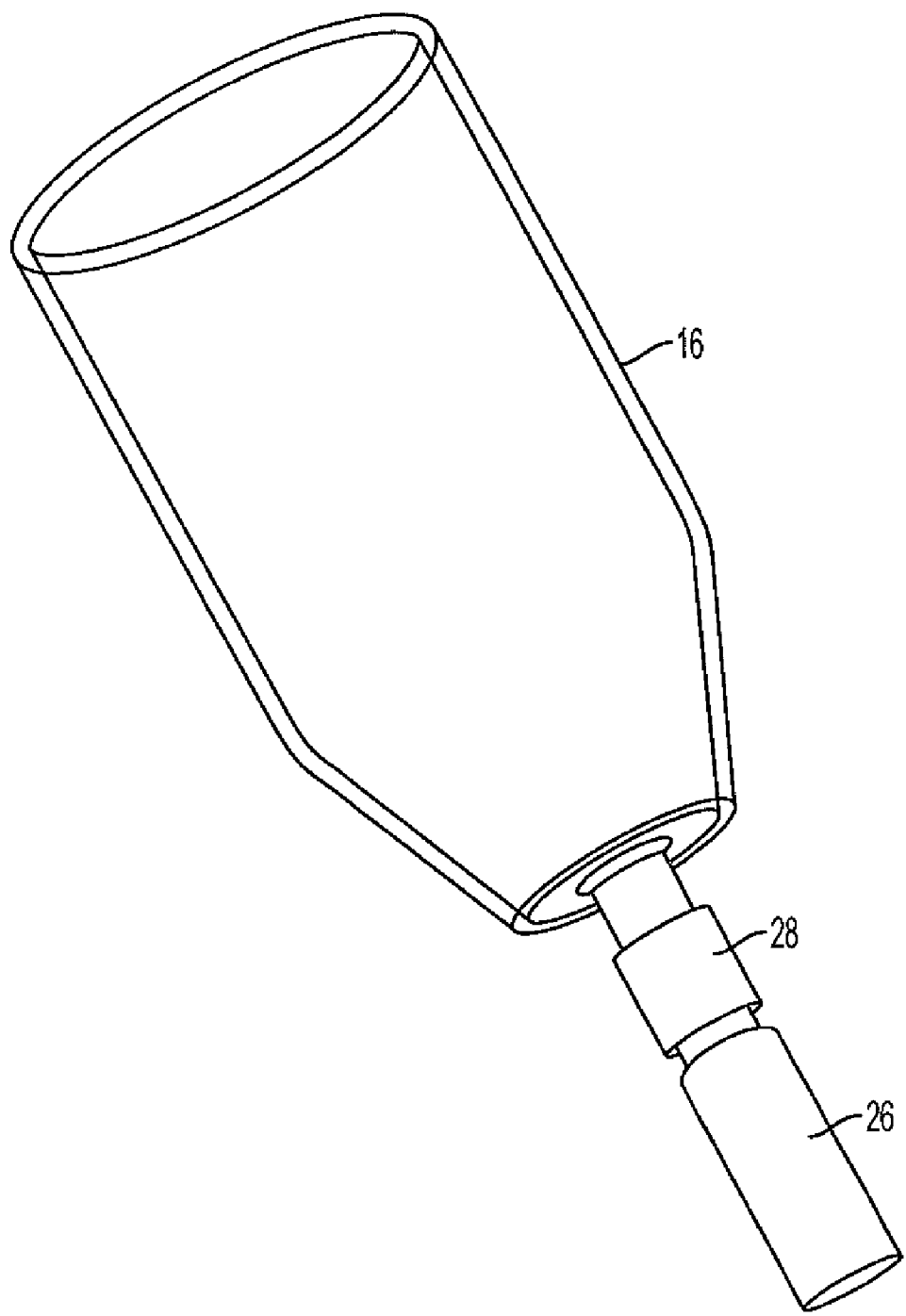
FIG. 2 shows an embodiment of a sample collection system consistent with the present invention.
Figure 3:
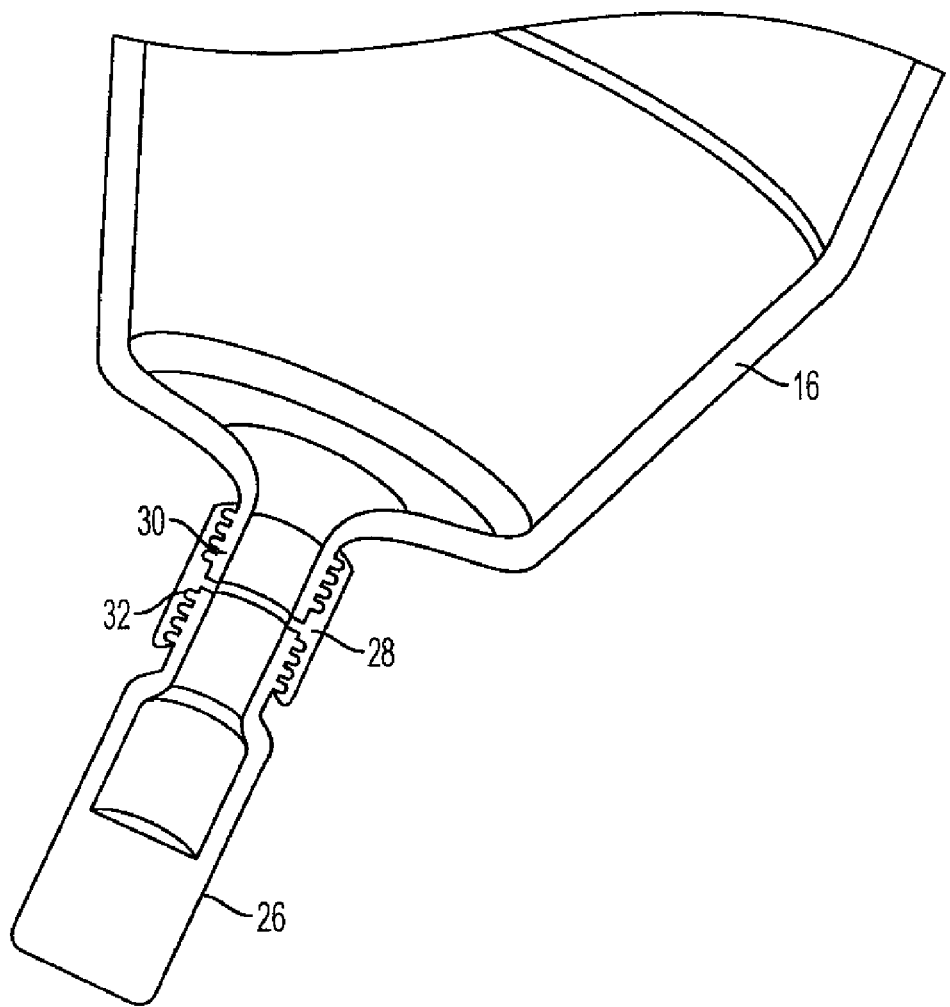
FIG. 3 is a partial sectional perspective view of an embodiment of a sample collection system consistent with the present invention.

Turning to FIGS. 2 and 3, an embodiment of a sample collection system, including an evaporation tube 16 coupled to a sample vial 26, is shown. The sample vial 26 may include, for example, a gas chromatography autosampler vial. A gas chromatography autosampler vial may contain a sample for gas chromatography analysis in an automated gas chromatography system. An autosample vial may therefore be understood as a vial that may be suitable for engagement with a robotic arm and/or suitable for use in a tray rotation technique, etc. Such vial may therefore have a threaded portion for a cap and may have an open hole for autosampler use or a solid cap for sample storage. Single piece polypropylene cap and membrane may also be utilized. It is also contemplated herein that the autosampler vials herein may include a crimp top, a snap seal vial or a shell vial. Furthermore, the autosampler vials herein may be of varying size and may utilize septums of appropriate chemical resistance.

The evaporation tube 16 may be connected to the sample vial 26 by a coupling 28. As the sample is processed by the evaporative concentrator system 10, the concentrated sample may be collected directly in the sample vial 26. Such direct collection of the sample in the sample vial 26 may eliminate the need for separately transferring the sample from the evaporation tube 16 to a sample vial 26, from which the sample may be analyzed. Accordingly, there may be a reduction in the time needed for preparing samples. The risk of losing the sample, e.g., via spillage, mishandling, etc., may be reduce or eliminated.

As shown, in one embodiment the evaporation tube 16 and the sample vial 26 may include exteriorly threaded necks 30, 32. The coupling 28 may include cooperating internal threads. The coupling 28 may, therefore secure the evaporation tube 16 and the sample vial 26 to one another. Additionally, the coupling 28 may generally align the necks 30, 32 of the evaporation tube 16 and sample vial 26 to enable the sample to flow from the evaporation tube 16 into the sample vial 26 without waste, contamination, etc. In various other embodiments, the coupling may include features other than threads for engaging the evaporation tube and sample vial. For example, the coupling and the evaporation tube may include cooperating precision tapers. Additionally, while the coupling may be produced from any suitable material, at least the surface of the coupling engaging the evaporation tube or the sample vial may include a deformable or resilient material, e.g., a plastic material, which may allow a press fit between the coupling and the evaporation tube or sample vial. For example, the resilient material may comprises a material that has a flexural modulus of less than about 300,000 psi and/or an elongation at break of greater than about 50%. The coupling may therefore include an elastomeric material (e.g. material with an elongation of greater than or equal to about 100%) and/or may include resiliently deformable features, such as ribs, etc., for releasably engaging the evaporation tube or sample vial.

Figure 4:
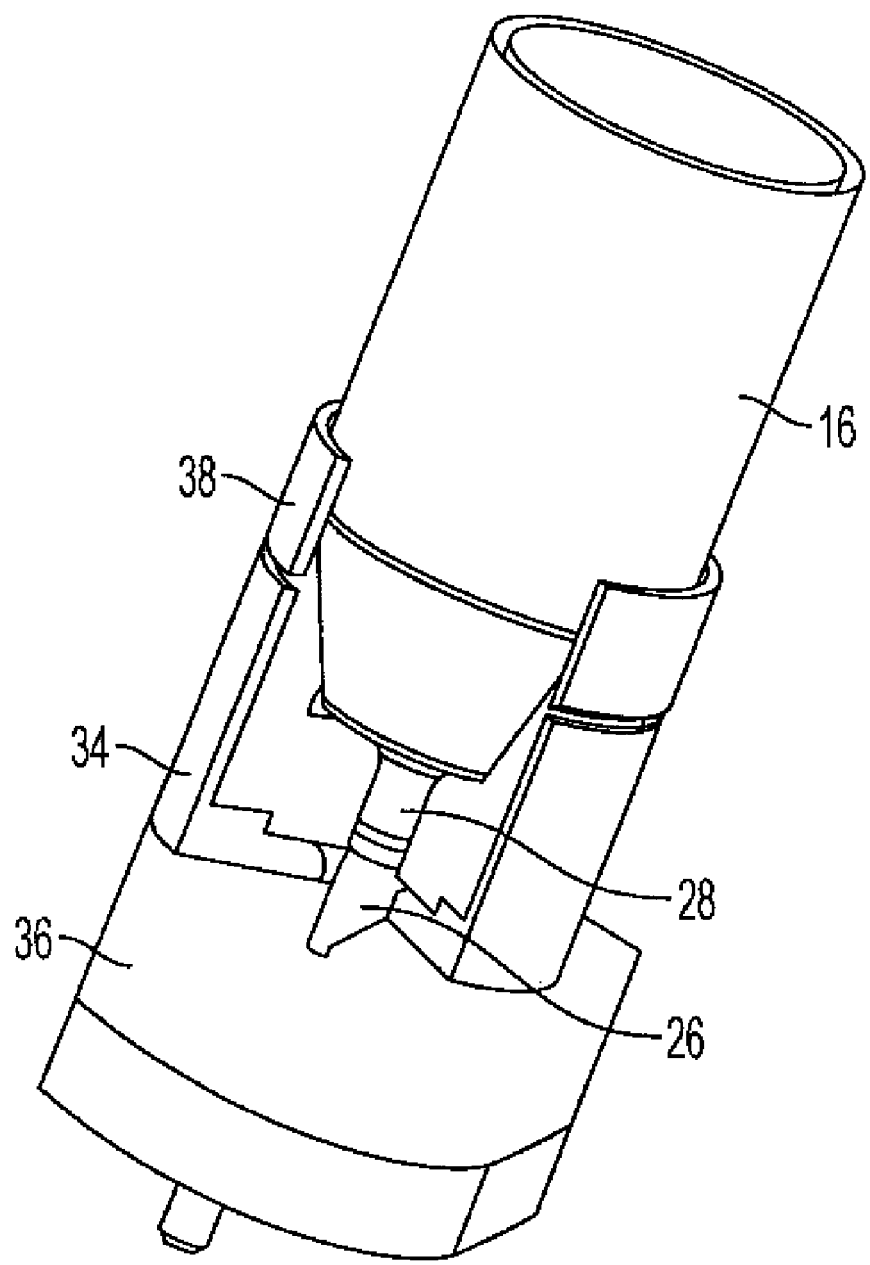
FIG. 4 is a partial cross-sectional illustration of an embodiment of a sample collection system consistent with the present invention.

Referring also to FIG. 4, the evaporation tube 16 and sample vial 26 may be supported in a cradle 34, e.g., during concentration of the sample, e.g., in an evaporative concentration system 10. As shown, the cradle 34 may support the evaporation tube 16 and sample vial 26 relative to a sensor housing 36. The sensor housing 36 may include one or more sensors that may detect various characteristics of a sample contained in the sample vial 26 during the evaporative concentration process. For example, one or more sensors may be provided for determining a fill level of the sample vial 26 for controlling the extent of the evaporative concentration to achieve a desired final sample volume. Various other characteristics of the sample, or of the sample vial, may also be detected.

As also shown, a cradle spacer 38 may be provided between at least a portion of the evaporation tube 16 and cradle 34. The cradle spacer 38 may have a generally complimentary shape relative to the evaporation tube 16, and may include an opening for receiving at least a portion of the coupling 28 and/or the sample vial 26. More than one cradle spacer may be provided allowing sample vials having different heights to be used, while still achieving a desired positioning of the sample vial relative to the sensor housing. For example, different spacers may maintain the evaporation tube 16 at different respective heights relative to the sensor housing.

It should be understood that, while the present invention has been described by reference to an exemplary embodiment thereof, the invention can be embodied otherwise without departing from the principles thereof, and such other embodiments are meant to come within the scope of the present invention.

What is claimed is:

1. An apparatus to provide a sample for analysis comprising:
    an open vessel to receive a solution of an analyte in a solvent, and to concentrate the analyte in the solvent, wherein the vessel comprises a first opening to receive the solution, an evaporation tube to concentrate the analyte and a second opening to provide a sample to a sample collection vial; and
    wherein the sample collection vial is connected to the vessel by a coupling; and
    wherein the sample collection vial comprises a vial to provide the sample to an analytical analysis system.

2. The apparatus of claim 1 wherein:
    wherein the first opening and the second opening are at opposing ends of the vessel.

3. The apparatus of claim 1 wherein:
    the sample collection vial comprises a gas chromatography vial.

4. The apparatus of claim 3 wherein:
    the gas chromatography vial comprises a gas chromatography autosampler vial and the analytical analysis system comprises an automated gas chromatography system.

5. The apparatus of claim 1 wherein:

the coupling comprises a first threaded portion to attach to a threaded portion of the vessel, and a second threaded portion to attach to a threaded portion of the sample collection vial.

6. The apparatus of claim 5 wherein:

the coupling first threaded portion comprises internal threads to attach to external threads of the vessel threaded portion and the coupling second threaded portion comprises internal threads to attached to external threads of the sample collection vial threaded portion.

7. The apparatus of claim 1 wherein:

the coupling comprises a resilient material.

8. The apparatus of claim 1 wherein:

the coupling comprises an elastomeric plastic material.

9. The apparatus of claim 1 wherein:

the coupling limits fluid communication of the sample collection vial to the vessel.

10. The apparatus of claim 1 further comprising:

a cradle to support at least one of the vessel and the sample collection vial.

11. The apparatus of claim 10 wherein:

the cradle includes an opening to receive at least a portion of the coupling and/or the sample collection vial.

12. The apparatus of claim 10 wherein:

the cradle includes one or more spacers to a provide for a height of the sample collection vial.

13. The apparatus of claim 1 further including:

a sensor to determine one or more characteristics of the sample in the sample collection vial.

14. The apparatus of claim 13 further including:

the sensor determines a fill level of the sample in the sample collection vial.

15. An apparatus to provide a sample for analysis comprising:

an open vessel;

a sample collection vial;

the open vessel to receive a solution of an analyte in a solvent, and to concentrate the analyte in the solvent, wherein the vessel comprises a first opening to receive the solution, an evaporation tube to concentrate the analyte and a second opening to provide a sample to the sample collection vial;

the sample collection vial connected to the vessel by a coupling, the coupling to transfer the sample from the vessel directly to the sample collection vial; and a cradle to support the vessel and including an opening to receive at least a portion of the coupling and/or sample collection vial.

16. The apparatus of claim 15 wherein:

the sample collection vial comprises a vial to provide the sample to an analytical analysis system.

17. The apparatus of claim 15 wherein:

the coupling comprises a first threaded portion to attach to a threaded portion of the vessel and a second threaded portion to attach to a threaded portion of the sample collection vial.

18. The apparatus of claim 15 wherein:

the coupling limits fluid communication of the sample collection vial to the vessel.

19. A method to provide a sample for analysis comprising:

providing an apparatus to provide a sample for analysis comprising:

an open vessel;

a sample collection vial;

the open vessel to receive a solution of an analyte in a solvent, and to concentrate the analyte in the solvent, wherein the vessel comprises a first opening to receive the solution, an evaporation tube to concentrate the analyte and a second opening to provide a sample to the sample collection vial;

the sample collection vial connected to the vessel by a coupling, the coupling to transfer the sample from the vessel directly to the sample collection vial;

a cradle to support the vessel and including an opening to receive at least a portion of the coupling and/or sample collection vial;

preparing the sample in the vessel; and transferring the sample from the vessel to the sample collection vial.

20. The method of claim 19 further including:

using a sensor to determine one or more characteristics of the sample in the sample collection vial.

* * * * *